(12) United States Patent
Immink et al.

(10) Patent No.: US 8,986,624 B2
(45) Date of Patent: Mar. 24, 2015

(54) MEASUREMENT DEVICE FOR BODY FLUID ANALYSIS

(75) Inventors: Albert Hendrik Jan Immink, Eindhoven (NL); Petrus Johannes Wilhelmus Van Lankvelt, Boekel (NL); Tom Philippe Jean Jacques Delaey, Mol (BE)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 13/128,184

(22) PCT Filed: Nov. 10, 2009

(86) PCT No.: PCT/IB2009/054982
§ 371 (c)(1),
(2), (4) Date: May 6, 2011

(87) PCT Pub. No.: WO2010/055464
PCT Pub. Date: May 20, 2010

(65) Prior Publication Data
US 2011/0206575 A1    Aug. 25, 2011

(30) Foreign Application Priority Data

Nov. 14, 2008  (EP) .................................. 08169151

(51) Int. Cl.
*G01N 33/00* (2006.01)
*G01N 21/13* (2006.01)

(52) U.S. Cl.
CPC ........ *G01N 21/13* (2013.01); *G01N 2201/0221* (2013.01); *G01N 2201/0256* (2013.01)
USPC ........... 422/403; 422/400; 422/401; 422/402; 422/68.1

(58) Field of Classification Search
USPC ........................ 422/403, 400, 401, 402, 68.1
See application file for complete search history.

(56) References Cited

U.S. PATENT DOCUMENTS

| | | | |
|---|---|---|---|
| 6,066,243 | A | 5/2000 | Anderson |
| 6,377,894 | B1 | 4/2002 | Deweese |
| 2006/0222567 | A1 | 10/2006 | Kloepfer |
| 2006/0275890 | A1 | 12/2006 | Neel |
| 2007/0233395 | A1 | 10/2007 | Neel |

FOREIGN PATENT DOCUMENTS

| | | |
|---|---|---|
| EP | 1736772 A1 | 12/2006 |
| FR | 2691248 A1 | 11/1993 |
| WO | 0007013 A2 | 2/2000 |
| WO | 03082091 A2 | 10/2003 |

*Primary Examiner* — Sam P Siefke

(57) ABSTRACT

A measurement device includes a housing and at least one display integrated in the housing. The housing includes a recess adapted for insertion of a cartridge into the housing to deliver a sample to be measured to the device. The recess has an opening at the front of the housing and a first part of the housing for insertion of the cartridge protrudes in a direction enclosing an angle with a second part of the housing.

15 Claims, 2 Drawing Sheets

MEASUREMENT DEVICE FOR BODY FLUID ANALYSIS

FIELD OF THE INVENTION

The present invention relates to a measurement device and a measurement method.

BACKGROUND OF THE INVENTION

The demand for biosensors measuring the amount or concentration of biological entities is increasingly growing these days. Usually, biosensors allow for the detection of a given specific molecule or target analyte within a small sample volume, wherein the amount of said molecule is typically small. For example, one may measure the amount of drugs or cardiac markers within saliva or blood. Therefore, label particles, for example super-paramagnetic beads, are used which bind to a specific binding site or active surface only, if the molecule to be detected is present within the sample. One recent technique to detect these label particles bound to the active surface is frustrated total internal reflection (FTIR). Therein, light is coupled into the disposable substrate such that it illuminates the active surface from the inside at an angle of total internal reflection. If no particles are present close to the active surface, the light is completely reflected. If, however, label particles are bound to said surface, the evanescent field extending in the sample fluid is scattered by or coupled into the super-paramagnetic label. A portion of the light is scattered into the sample or absorbed by the particle and thus the amount of light reflected by the surface is decreased. By measuring the intensity of the reflected light with an optical detector, it is possible to estimate the amount of particles bound to the surface. This allows for an estimate of the amount of the specific molecules of interest present within the sample fluid. For point of care applications biosensors having small measures for a comfortable use are aimed for, e.g. biosensor devices held in a hand. Other biosensor devices are rather designed for use on desk top, these are mostly immobile on the desk top surface and for laboratory use, commonly operated by skilled personnel. Measurement devices comprising biosensors now are designed either for handheld use in point of care applications or for laboratory use.

SUMMARY OF THE INVENTION

It is therefore an object of the present invention to provide a measurement device and a method which provide a flexible and user-friendly use in both a handheld situation for point of care and a desktop situation for use in e.g. a laboratory.

Provided is a measurement device with a housing and at least one display integrated in the housing, wherein the housing comprises a recess adapted for insertion of a cartridge into the housing to deliver a sample to be measured to the device, wherein the recess has an opening at the front of the housing and a first part of the housing for insertion of the cartridge protrudes in a direction enclosing an angle with a second part of the housing. The cartridge after insertion into the first part of the housing is nearly completely or completely enclosed by the first part of the housing. One front side of the cartridge next to the opening of the recess is still visible after insertion and can also protrude over the recess. This means the first part of the housing terminates with one front side of the cartridge or the front side projects somewhat over the first part of the housing. The cartridge does not add to the extent of the measurement device, therefore handling is improved. The device structure allows the display to be easily visible by the user and insertion of the cartridge is easily accessible and visible during use. Concurrently a stable positioning of the measurement device onto a placement area is achieved. The measurement device is usable in a mobile operation mode as hand held device and also in an immobile operation mode as desk top device. The recess for insertion of the cartridge in the first part being distant from the desk top prevents dust and dirt to enter the housing and impairing the sensitive measurement of the sample.

In one example of the invention the measurement device the angle enclosed between the first part of the housing for insertion of the cartridge and the second part of the housing lies in a range between roughly 30° and 150°.

In a further example of the invention the first part of the housing of the measurement device has at one end a slanted surface to fit onto a placement area for positioning the measurement device for a stationary readout of the display of the measurement device and the second part of the housing is adapted to fit into a hand of a user for a non-stationary readout of the measurement device with the first part of the housing serving as the ending of the housing to abut the hand of the user. The handling of the measurement device is facilitated hereby.

In a further example of the invention the first part of the housing comprises besides the removable cartridge a detection device for detection of the sample delivered by the cartridge, and the second part of the housing comprises besides the display electronic circuits for transferring the measurement signals and calculating results on basis of the measurement signals, and an energy supply for supplying the measurement device with electrical power. The arrangement described leads to a device shape which enables the device to be used in mobile operation as hand held device as well as table top use.

In a further example of the invention a printer is integrated in the measurement device for printing the measurement results in case the sample contains a certain substance in a certain amount or concentration. When the measurement reveals that the sample of the person to be inspected is positive the measurement results are printed on paper for further procedure and as evidence. The printed paper is removable from the measurement device.

These and other aspects of the invention will be apparent from and elucidated with reference to the examples described hereinafter.

DETAILED DESCRIPTION OF EMBODIMENTS

Figure 1:
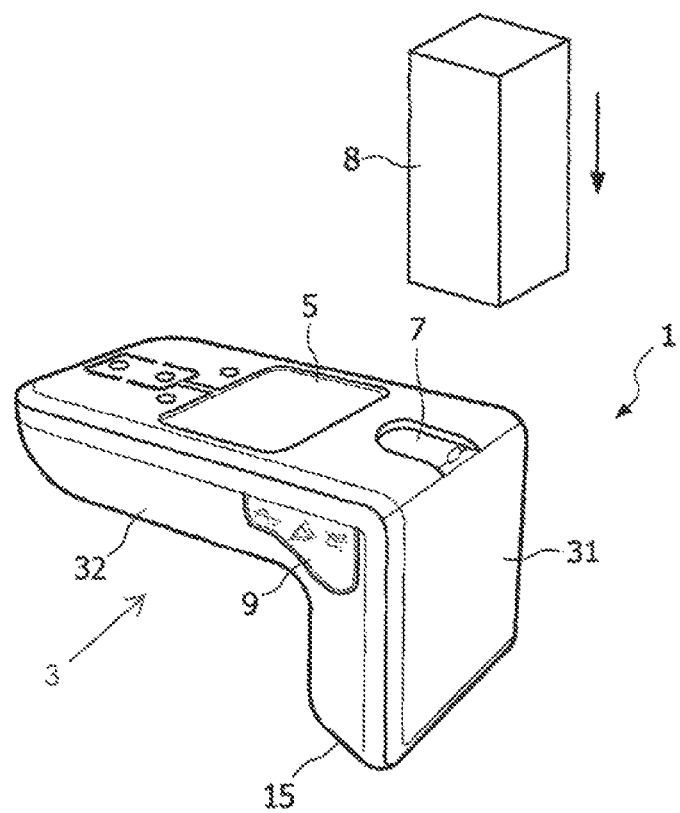
FIG. 1 schematically shows a view of an example of a measurement device with a cartridge to be placed into the housing of the measurement device, FIG. 2 schematically shows a top view of the measurement device according to FIG. 1 showing essentially the second part of the housing with display and operator interface with buttons to operate the device, FIG. 3 schematically shows a bottom view of the measurement device according to FIG. 1 and FIG. 2 showing the second part of the housing and a bottom view of the first part of the housing which accommodates the cartridge at the top of the drawings, FIG. 4 schematically shows a side view of the measurement device according to FIG. 1 showing also a flexible cover flap that covers the electrical interface connectors (like power, serial and USB connectors)

FIG. 1 schematically shows a view of an example of the invention of a measurement device 1 having a housing 3 comprising a first part 31 which lies in a line perpendicular to the display plane. The first part 31 of the measurement device 1 possesses an angle with regard to the second part 32 of the measurement device 1, in this example the angle is 90°. The second part 32 of the measurement device 1 lies in a roughly horizontal line to the display plane and has an integrated display 5 for displaying several measurement results. The housing 3 has a recess 7 formed to accommodate a disposable cartridge 8 within the first part 31 of the housing 3, whereby the recess 7 protudes through the first part 31 of the housing 3 starting from an opening shown in FIG. 1. The cartridge 8 is depicted schematically above the measurement device 1 with an arrow indicating the direction of insertion into the housing 3. The cartridge 8 serves for the examination of a liquid or solid sample, wherein said sample may for example be a biological substance, e.g. saliva, blood, urine or some other body fluid, or a material taken from the environment, e.g. from the soil, water, or food. The cartridge 8 can comprise a sample collection element for picking up a sample to be examined from its place of origin. The sample collection element may for example comprise a swab for collecting body fluid, e.g. saliva from the mouth of a patient. The cartridge 8 further comprises a sensor element for sensing a parameter of interest of a sample to be examined, for instance by means of optical detection means. The parameter of interest may particularly be the presence and possibly also the quantity or concentration of a particular target substance in the sample, for example the presence of a drug in saliva to be displayed on display 5. The cartridge 8 can further comprise a sample transportation mechanism for transporting picked up sample from the sample collection element to the sensor element. The sample transportation mechanism will typically perform some mechanical or even chemical preprocessing with the picked up sample during its transportation, for example a thorough mixing of the sample with a solvent such that well-defined conditions are assumed at the sensor element. After insertion into the measurement device 1 the cartridge 8 is releasably engaged to the measurement device 1. Cartridge 8 is preferably designed for a one-time use.

Figure 2:
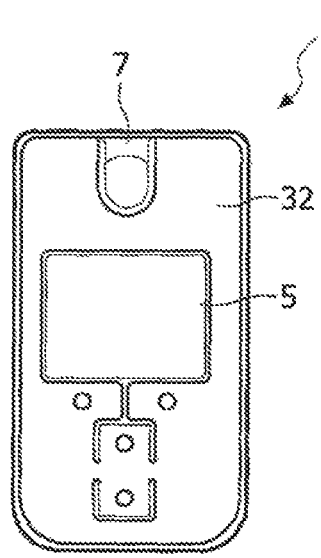
Figure 3:
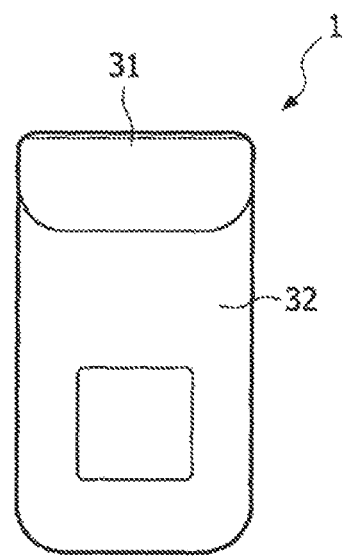

FIG. 2 schematically shows a top view of the measurement device 1 according to FIG. 1 showing essentially the second part 32 of the housing 3 with the display 5 giving the user the results of the measurements taken. On top of FIG. 2 the opening of the recess 7 for insertion of the cartridge 8 is shown. In this view the recess 7 projects into the image plane. Furthermore, the drawing shows the operator interface comprising buttons for operating the measurement device. FIG. 3 schematically shows a bottom view of the measurement device 1 according to FIG. 1 and FIG. 2 showing the second part 32 of the housing 3 and a bottom view of the first part 31 of the housing 3 at the top to accommodate the cartridge 8. In FIG. 2, showing the view as seen by a user in operation, it can be seen that the user has an accessible and clearly visible opening of the recess 7 as a cartridge entrance slot.

Figure 4:
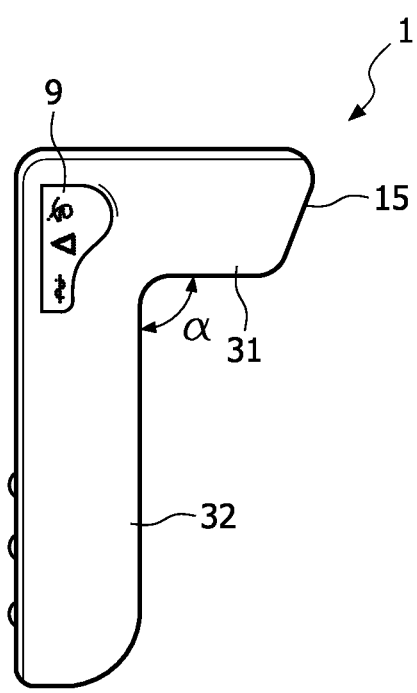
Figure 5:
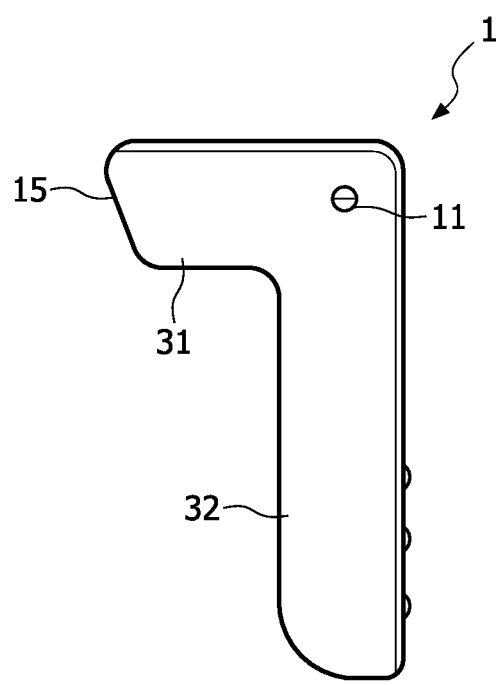
FIG. 5 shows a view similar to FIG. 4 rotated to show the opposite side of the measurement device also depicting a power button of the measurement device.

FIG. 4 schematically shows a side view of the measurement device 1 according to FIG. 1 showing also a flexible cover flap 9 that covers the electrical interface connectors, like power supply, serial and USB connectors. Shown in FIG. 4 are buttons protruding from the housing 3 to operate the measuring device 1. FIG. 5 shows a rotated view similar to FIG. 4 to show the opposite side of the measurement device 1 also depicting a power button 11 of the measurement device 1. The surface according to FIG. 4 being accessible, especially when held in a left hand of a user, can further comprise electrical connectors, e.g. USB (Universal Serial Bus), power connector, or a connector for a serial printer. By this an easy access for insertion of plugs and cables is achieved, especially the right hand of the user feeding the electrical connectors when holding the measurement device 1 with the left hand. FIG. 4 and FIG. 5 are shown in a view according to a handheld operation mode described below, the first part 31 of the housing 3 on top and the second part 32 projecting downwards. In the second desk-top operation mode the housing 3 is tilted around the bottom of the second part 32 in the direction of the first part 31, so the slanted surface 15 fits the desk-top. The structure of the measurement device 1 prevents a slip of the measurement device 1 through the hands of a user. The first part 31 of the measurement device 1 serves as a means for preventing the measurement device 1 to fall out of the users hand, as the first part 31 abuts against the users hand in operation and catches the measurement device 1. The manipulation of the measurement device 1 is improved, e.g. in case the cartridge 8 is inserted as depicted in FIG. 1. Manipulation is especially improved in case the user wears gloves, as in police operation, or in situations where the outside of the housing 3 of the measurement device 1 is slippery, e.g. in case of rain.

The measurement device 1 with cartridge 8 is used in two very different scenarios. The first scenario where the measurement device 1 is held in one hand of the user and the cartridge 8 is inserted with the other hand. The measurement device 1 fits in the users hand in a robust way, i.e. it does not fall out easily, e.g. when inserting the cartridge 8. Concurrently, the measurement device 1 allows the police officer to watch continuously the person-under-test while performing the test to avoid dangerous situations when the person-under-test is suspected to attack the police officer. This scenario for example followed during through-the-window roadside drug testing as described below. In a traffic control a police officer stops a driver of an automobile at the road-side, unpacks and inserts the cartridge 8 into the measurement device 1. Part of the cartridge 8 is a sample taking unit (not shown) for collecting a sample from the driver, which upon taking the sample, here saliva, is again put into the cartridge 8 for measuring certain substances within the sample, in this example drugs of abuse that are illegal in many countries. The first part 31 of the housing 3 encompasses the removable cartridge 8 and a detection device for detection of the sample delivered by the cartridge 8. The detection device is for instance a sensitive optical detection device for detecting substances at an assay, which detection device is known in the art. The second part 32 of the housing 3 comprises the display 5, electronic circuits for transferring the measurement signals from the detection device and calculating results on basis of the measurement signals. Further, the second part 32 of the housing 3 comprises an energy supply for supplying the measurement device 1 with electrical power, for instance a battery. Further applicable energy supplies comprise photovoltaic cells or fuel cells. The structure as shown and described with the several parts of the measurement device 1 divided to the first part 31 and the second part 32 allows the housing 3 of the measurement device 3 to be in a form which is manageable in mobile use. Especially the cartridge 8 accommodated essentially in the first part 31 of the housing 3 when inserted reaches this effect. The length and size of the housing 3 is crucially reduced by the structure disclosed, facilitating and making possible the handling and storing of the measurement device 1 beyond laboratory and desktop use.

Regarding the second scenario the measurement device 1 is placed with the essentially slanted surface 15 at the bottom of the first part 31 of the housing 3 onto a placement area (not shown), generally a table. The angle enclosed between the first part 31 of the housing 3 for insertion of the cartridge 8 and the second part 32 of the housing 3 lies in a range between roughly 30° and 150°, in the Figs an angle of about 90° is depicted. Here, the first part 31 of the housing 3, more precisely the far ending of the first part 31 with the slanted surface 15, is used as a bearing for positioning the measurement device 1 onto a placement area. Placed into this position the housing 3 fits with one ending surface of the second part 32, preferably also slanted, and with the other ending surface of the first part 31, the slanted surface 15 that is more distant to the user, at the placement area. The measurement device 1 in this second scenario put onto a placement area is used in a stationary way, the display 5 of the measurement device 1 is read out stationary without manual handling. The second part 32 of the housing 3 standing upright with a certain angle with regard to the placement area allows a clear view on the display 5 while the user is still able to watch the person-under-test during the complete procedure of reading-out. The user having the possibility to read-out and watch simultaneously is of importance in police operation for drug of abuse testing to assure the safety of the user, the police officer, against attacks. The structure of the housing 3 allows insertion of the cartridge 8 with one hand of the user without holding the measurement device 1. The forces imposed on the housing 3 by insertion of the cartridge 8 are transferred to the placement area due to the angle-of-insertion with respect to the placement area. A soft-material, e.g. rubber inlay mounted at the bottom of the housing 3, i.e. at the slanted surface 15 of housing part 31 transfers the forces generated by inserting the cartridge 8. Furthermore, such a rubber inlay reduces acceleration forces when the measurement device 1 is placed onto the placement area. Low acceleration forces are especially important as a fluidic stop within the cartridge 8 to control the sample flow needs to withstand these acceleration forces in order to stop the sample fluid in a robust way. The design as described eliminates the need for a separate bearing at the housing 3 for placing the measurement device 1 at a placement area to thereby reduce costs of the measurement device 1.

The described structure allows the sensor element or read-out module to be integrated with the electronic circuits, the energy supply, and the display in a housing 3 that is appropriate as a hand-held device. Integrating all items in a box-shape would make it either too thick, too wide, or too long to handle it conveniently in a mobile situation. The read-out module is especially large because the cartridge 8 for accepting and measuring the sample, e.g. saliva, is rather long to allow squeezing of the long sample taking unit of the cartridge 8 in the squeeze tube that is integrated with the disposable cartridge 8. A long sample taking unit is required to collect saliva from the mouth in an efficient way. The long sample taking unit is accommodated in the first part 31 of the housing 3 when the cartridge 8 is inserted.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. Any reference signs in the claims should not be construed as limiting the scope.

The invention claimed is:

1. In combination, a measurement device and a cartridge which delivers a biological sample to be measured to the measurement device, the measurement device comprising:
    a housing having a first part and a second part; and
    at least one display integrated in the housing,
        wherein the second part has a recess with an opening for insertion of the cartridge into the recess, the recess protruding through the first part of the housing to deliver the biological sample to be measured to the first part,
        wherein the first part encloses an angle with the second part of the housing and protrudes away from the second part far enough to fit and abut a hand of a user for being held by the hand of the user,
        wherein the cartridge after insertion into the first part is nearly completely or completely enclosed by the first part, and
        wherein the first part of the housing comprises a detection device which detects a parameter of the biological sample delivered by the cartridge.

2. The measurement device according to claim 1, wherein the angle enclosed between the first part of the housing for insertion of the cartridge and the second part of the housing lies in a range between 30° and 150°.

3. The measurement device according to claim 1, wherein the first part of the housing has at one end a slanted surface to fit onto a placement area for positioning the measurement device for a stationary readout of the display of the measurement device and the second part of the housing is adapted to fit into the hand of the user for a non-stationary readout of the measurement device with the first part of the housing serving as an ending of the housing to abut the hand of the user.

4. The measurement device according to claim 3, wherein an angle of the second part of the housing with regard to the placement area lies in a range between 10° and 60°.

5. The measurement device according to claim 1, wherein the second part of the housing further comprises electronic circuits for transferring measurement signals from the detection device and calculating results based on the measurement signals, and an energy supply for supplying the measurement device with electrical power.

6. The measurement device according to claim 1, further comprising a printer integrated in the measurement device tor printing measurement results.

7. The measurement device according to claim 3, wherein the slanted surface comprises a soft-material inlay that transfers forces imposed on the measurement device to the placement area at which the measurement device is placed.

8. The measurement device according to claim 1, wherein the angle enclosed between the first part of the housing for insertion of the cartridge and the second part of the housing lies in a range between 60° and 130°.

9. The measurement device according to claim 1, wherein the angle enclosed between the first part of the housing for insertion of the cartridge and the second part of the housing lies in a range between 80° and 100°.

10. The measurement device according is claim 3, wherein an angle of the second part of the housing with regard to the placement area lies between 20° and 50°.

11. A measurement device comprising:
- a housing having a first part and a second part; and
- a display integrated in the housing,
  - the second part having a recess with an opening for insertion of an associated cartridge into the recess in the second part, the recess protruding through the first part of the housing to deliver a biological sample to be measured to the first part,
  - the first part enclosing an angle with the second part of the housing and protrudes away from the second part far enough to fit and abut a hand of a user for being held by the hand of the user,
  - the cartridge after insertion into the first part being nearly completely or completely enclosed by the first part,
  - the first part of the housing comprising a detection device configured to detect a parameter of biological sample delivered by the cartridge, and
  - the second part including the display, the display being on a same plane as the opening.

12. The measurement device of claim 1, wherein the first part is perpendicular to the second part for insertion of the cartridge in a vertical direction into the recess of the first part when the second part is in a horizontal direction.

13. The measurement device of claim 1, wherein the detection device comprises an optical detection means.

14. The measurement device of claim 1, wherein the first part lies in a line perpendicular to the plane.

15. The measurement device of claim 1, further comprising an energy supply for supplying the measurement device with electrical power, the energy supply comprising a battery.

* * * * *